United States Patent [19]

Gilligan et al.

[11] 4,411,837

[45] Oct. 25, 1983

[54] HALO, NITRO, AND HALONITRO S-ALKYL THIOCARBONATES

[75] Inventors: William H. Gilligan, Ft. Washington, Md.; Scott L. Stafford, Petersburg, Ak.

[73] Assignee: The United States of America as represented by the Secretary of the Navy, Washington, D.C.

[21] Appl. No.: 354,261

[22] Filed: Mar. 3, 1982

Related U.S. Application Data

[62] Division of Ser. No. 224,776, Jan. 13, 1981, Pat. No. 4,332,744.

[51] Int. Cl.[3] .......... C07C 154/00

[52] U.S. Cl. .......... 260/455 B; 149/88

[58] Field of Search .......... 260/455 B, 463

[56] References Cited

U.S. PATENT DOCUMENTS 3,338,947 8/1967 Berezin et al. .......... 260/455 B

*Primary Examiner*—Henry R. Jiles
*Assistant Examiner*—Robert C. Whittenbaugh
*Attorney, Agent, or Firm*—R. S. Sciascia; A. L. Branning; R. D. Johnson

[57] ABSTRACT

Unsymmetrical carbonates of the formula

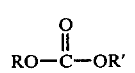

[I]

are prepared by the following reaction sequence (1)

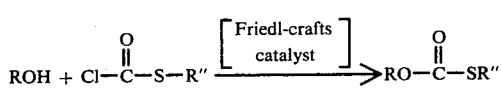

[II] [III] [IV]

(2)

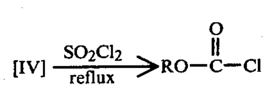

[V]

-continued (3)

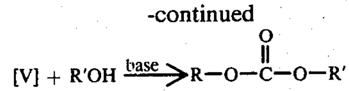

[VI] [I]

where R and R' can each be $—CH_2C(NO_2)_3$, $CH_2CF(NO_2)_2$, $—CH_2CF_2(NO_2)$, $—CH_2CCl(NO_2)_2$, $—CH_2CF_3$, $—CH_2CCl_3$, $—CH_2C(NO_2)_2CH_3$, or $—CH_2CF_2CF_2H$, provided that $R \neq R'$ and wherein R'' is a lower alkyl group of from 1 to 6 carbon atoms.

Also included are symmetrical 1,3-bis(halo- and nitroalkyl carbonyldioxy)-2,2-dinitropropanes of the formula

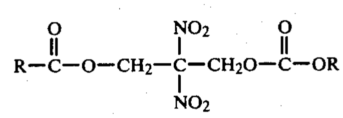

[VII]

which are synthesis by the following reaction sequence (a)

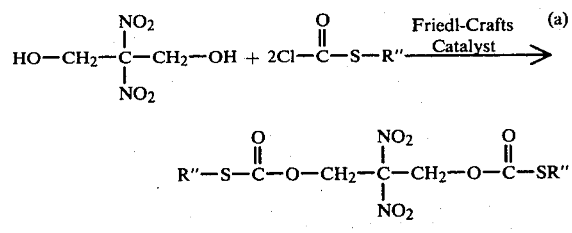

[IX]

b.

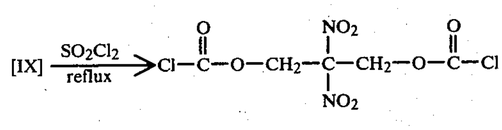

[X]

c.

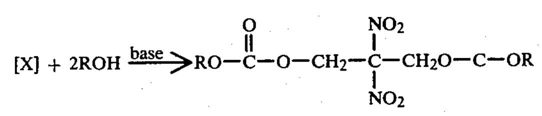

[VII]

wherein R and R'' are as defined above.

The carbonates of this invention are useful as energetic additives to propellants and explosive.

13 Claims, No Drawings

HALO, NITRO, AND HALONITRO S-ALKYL THIOCARBONATES

This is a division of application Ser. No. 224,776, filed Jan. 13, 1981, now U.S. Pat. No. 4,332,744.

BACKGROUND OF THE INVENTION

This invention relates to organic carbonates and more particularly to nitro substituted organic carbonates.

In order to prepare unsymmetrical carbonates, it is necessary to react a chloroformate of an alcohol with a second alcohol. The general method for preparing chloroformates is to react an alcohol with an excess of phosgene (poisonous gas) in the presence of a base as an acid acceptor. Inevitably a greater or lesser amount of the carbonate is formed, as a by-product, which lowers the yield and requires separation of the product. In addition, nitroalcohols in the presence of base, have a tendency to deformylate, which also lowers the yield of chloroformate. A third factor is that nitro substituted diols such as 2,2-dinitropropan-1,3-diol form as major products linear carbonates and cyclic carbonates.

SUMMARY OF THE INVENTION

An object of this invention is to provide new organic compounds.

Another object of this invention is to provide new explosive materials.

A further object of this invention is to provide unsymmetrical polynitrocarbonates.

Still another object is to provide a method of synthesizing unsymmetrical polynitrocarbonates.

Yet a further object of this invention is to provide novel symmetrical, 1,3-bis(halo- and nitroalkyl carbonyldioxy)-2,2-dinitropropanes.

Still a further object of this invention is to provide a method of synthesizing novel symmetrical 1,3-bis(halo- and nitroalkyl carbonyldioxy)-2,2-dinitropropanes.

These and other objects of this invention are achieved by providing (1) novel unsymmetrical polynitrocarbonates of the formula

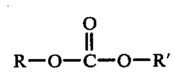

by the following reaction sequence

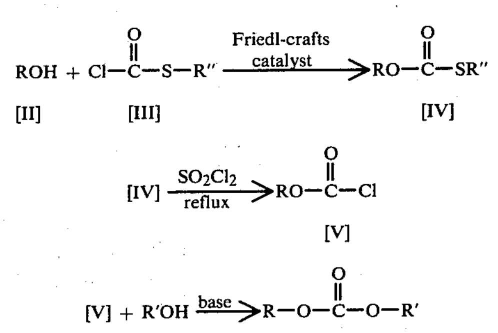

(1) [II] [III] [IV]

(2) [V]

(3) [VI] [I]

wherein R≠R' and wherein R and R' are each selected from the group consisting of $-CH_2C(NO_2)_3$, $CH_2CF(NO_2)_2$, $-CH_2CF_2(NO_2)$, $-CH_2CCl(NO_2)_2$, $-CH_2CF_3$, $-CH_2CCl_3$, $-CH_2C(NO_2)_2CH_3$, and $-CH_2CF_2CF_2H$, and wherein R'' is a lower alkyl of from 1 to 6 carbon atoms; and (2) symmetrical 1,3-bis(-halo- and nitroalkyl carbonyldioxy)-2,2-dinitropropanes of the formula

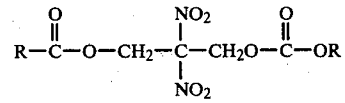

[VII]

which are synthesized by the following reaction sequence

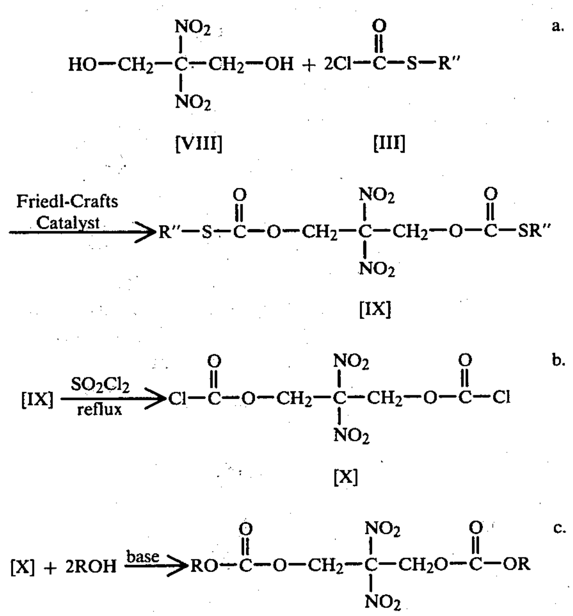

a. [VIII] [III] [IX]

b. [X]

c. [VII]

wherein R and R'' are as defined above.

The carbonates of this invention are useful as energetic additives to propellants and explosives.

DETAILED DESCRIPTION OF THE PREFERRED EMBODIMENT

The reaction sequences of this invention summarized as follows:

| STEP | UNSYMMETRICAL | SYMMETRICAL |
| --- | --- | --- |
| | 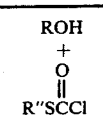 | 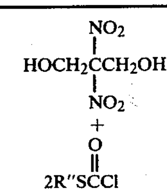 |
| (1) | Freidl-Crafts Catalyst | Freidl-Crafts Catalyst |
| | 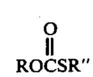 | 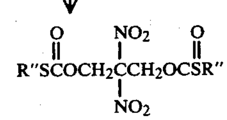 |

-continued

| STEP | UNSYMMETRICAL | SYMMETRICAL |
| --- | --- | --- |

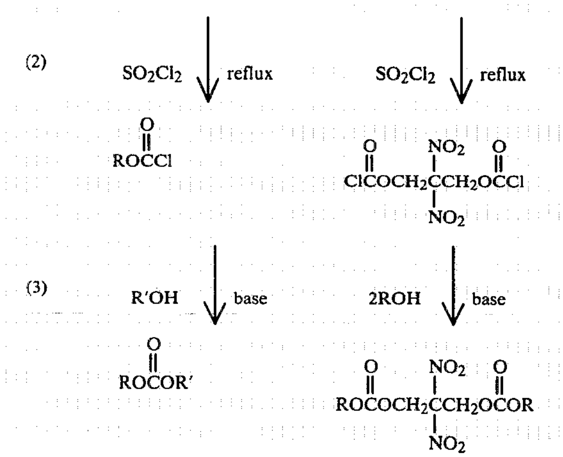

wherein R≠R' and R and R' can be $—CH_2C(NO_2)_3$, $—CH_2CF(NO_2)_2$, $—CH_2CF_2(NO_2)$, $—CH_2CCl(NO_2)_2$, $—CH_2CF_3$, $—CH_2CCl_3$, $—CH_2C(NO_2)_2CH_3$, and $—CH_2CF_2CF_2H$, and wherein R'' is a lower alkyl group of from 1 to 6 carbon atoms, but preferably a lower alkyl of from 1 to 3 carbon atoms.

The alcohols ROH and R'OH, which may be used in the synthesis are
2,2,2-trinitroethanol,
2-fluoro-2,2-dinitroethanol,
2,2-difluoro-2-nitroethanol,
2-chloro-2,2-dinitroethanol,
2,2,2-trifluoroethanol,
2,2,2-trichloroethanol,
2,2-dinitropropanol, and
2,2,3,3-tetrafluoropropanol.

Obviously, for unsymmetrical carbonates ROH must not be the same as R'OH. Note that the alcohol used in step (1) for the production of symmetrical 1,3-bis(halo and nitroalkyl carbonyldioxy)-2,2-dinitropropanes is 2,2-dinitropropan-1,3-diol.

The syntheses of the unsymmetrical and the symmetrical carbonates differ in the combination of alcohols used, but the same reaction conditions are used.

The solvents used in all reaction steps must be inert. Examples of suitable solvents are methylene chloride, chloroform, 1,2-dichloroethane, and benzene.

In step (1) a Friedl-Crafts catalyst was used in a nonbasis solution. Examples of suitable catalysts are ferric chloride, stannic chloride, titanium tetrachloride, and zinc chloride. Anhydrous ferric chloride was used in the examples 1–9.

Examples 1, 2, and 3 illustrate that the reaction between the alcohol and the alkyl chlorothiolformate is vigorous at ambient temperature in the presence of the catalyst (anhydrous $FeCl_3$). The reaction mixtures were stirred at ambient temperature for 30 to 60 minutes and yields of 90 percent or more were obtained.

The general formulas of the products of step (1) are

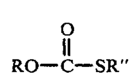

for the unsymmetrical synthesis and

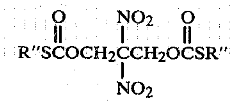

for the symmetrical synthesis. Because of the commercial availability of S-ethyl chlorothiolformate, the following products should be easiest to produce
S-ethyl 2,2,2-trinitroethyl thiolcarbonate,
S-ethyl 2-fluoro-2,2-dinitroethyl thiolcarbonate
S-ethyl 2,2-fluoro-2-nitroethyl thiolcarbonate,
S-ethyl 2-chloro-2,2-dinitroethyl thiolcarbonate,
S-ethyl 2,2,2-trifluoroethyl thiolcarbonate,
S-ethyl 2,2,2-trichloroethyl thiolcarbonate,
S-ethyl 2,2-dinitropropyl thiolcarbonate,
S-ethyl 2,2,3,3-tetrafluoropropyl thiolcarbonate, and finally the
Bis(S-ethyl thiolcarbonate) of 2,2-dinitropropan-1,3-diol,

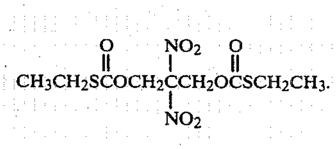

In step (2) the alkyl thiolcarbonate is refluxed with an excess of sulfuryl chloride ($SO_2Cl_2$) in an inert solvent until the alkyl thiolcarbonate is converted to the corresponding chloroformate. In Examples 4, 5, and 6, six hours of refluxing produced the products in good yield.

For reaction step (2) the general formula for the product of the unsymmetrical process is

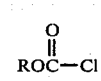

wherein R is as defined above. More specifically the compounds are
2,2,2-trinitroethyl chloroformate,
2-fluoro-2,2-dinitroethyl chloroformate,
2,2-difluoro-2-nitroethyl chloroformate,
2-chloro-2,2-dinitroethyl chloroformate,
2,2,2-trifluoroethyl chloroformate,
2,2,2-trichloroethyl chloroformate,
2,2-dinitropropyl chloroformate, and
2,2,3,3-tetrafluoropropyl chloroformate.

The product of the symmetrical process is

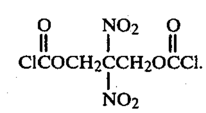

In step (3) the chloroformate is reached with an alcohol to produce the product carbonate. As illustrated by examples 7, 8, and 9, the reaction mixture should be cooled and the addition rate of the alcohol to the chloroformate should be adjusted so that the reaction mixture does not overheat. A base, such as pyridine, is added to the mixture to act as an acid acceptor for the HCl generated by the reaction.

In the case of the unsymmetrical synthesis the general reaction of step (3) is

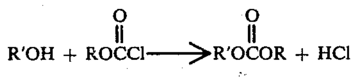

wherein R and R' are as defined above and R≠R'.

Preferred carbonates include 2-fluoro-2,2-dinitroethyl-3,3,3-trinitroethylcarbonate
2,2-difluoro-2-nitroethyl-3,3,3-trinitroethylcarbonate,
2-chloro-2,2-dinitroethyl-3,3,3-trinitroethylcarbonate,
2,2-dinitropropyl-3,3,3-trinitroethylcarbonate,
2,2-difluoro-2-nitroethyl-3-fluoro-3,3-dinitroethylcarbonate,
2-chloro-2,2-dinitroethyl-3-fluoro-3,3-dinitroethylcarbonate,
2,2-dinitropropyl-3-fluoro-3,3-dinitroethylcarbonate,
2-chloro-2,2-dinitroethyl-3,3-difluoro-3-nitroethylcarbonate,
2,2-dinitropropyl-3,3-difluoro-3-nitroethylcarbonate, and
2,2-dinitropropyl-3-chloro-3,3-dinitroethylcarbonate.

The general reaction of step (3) for the symmetrical 1,3-bis(halo- and nitroalkyl carbonyldioxy)-2,2-dinitropropanes synthesis is

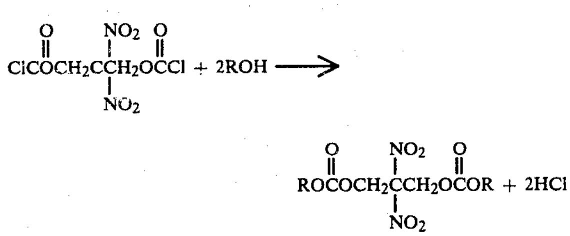

where R is as defined above. Specifically the symmetrical 1,3-bis(halo- and nitroalkyl carbonyldioxy)-2,2-dinitropropanes are 1,3-bis(3,3-trinitroethyl carbonyldioxy)-2,2-dinitropropane,
1,3-bis(3-fluoro-3,3-dinitroethyl carbonyldioxy)-2,2-dinitropropane,
1,3-bis(3,3-difluoro-3-nitroethyl carbonyldioxy)-2,2-dinitropropane,
1,3-bis(3-chloro-3,3-dinitroethyl carbonyldioxy)-2,2-dinitropropane,
1,3-bis(3,3,3-trifluoroethyl carbonyldioxy)-2,2-dinitropropane,
1,3-bis(3,3,3-trichloroethyl carbonyldioxy)-2,2-dinitropropane,
1,3-bis(3,3-dinitropropyl carbonyldioxy)-2,2-dinitropropane, and
1,3-bis(3,3,4,4-tetrafluoropropyl carbonyldioxy)-2,2-dinitropropane.

The three step process used to synthesis the unsymmetrical carbonates of this invention, may be used to synthesis a wide variety of unsymmetrical carbonates. However, the alcohol used in step (1) to prepare the S-alkyl thioformate should have at least one electronegative substituent, such as $NO_2$, F, etc. The presence of the substituent inhibits chlorination of the functional group, which otherwise would give rise to side-products.

The general nature of the invention having been set forth, the following examples are presented as specific illustrations thereof. It will be understood that the invention is not limited to these examples but is susceptible to various modifications that will be recognized by one of ordinary skill in the art.

EXAMPLE 1

S-ethyl 2,2,2-trinitroethyl thiolcarbonate

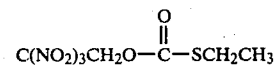

To a stirred solution of 9.2 g of 2,2,2-trinitroethanol in 10 ml of 1,2-dichloroethane was added 6.5 ml of ethyl chlorothiolformate and one ml of a 50% anhydrous ferric chloride solution in nitromethane. A vigorous reaction immediately ensued. The solution was stirred for one hour and then taken up in methylene chloride and washed consecutively with dilute hydrochloric acid and five 60 ml portions of water. After drying with anhydrous magnesium sulfate, the organic solution was filtered and the solvents removed in vacuo. The residue was crystallized from chloroform/hexane solution to give 12.52 g (90%) of the title compound: m.p. 36°. H-NMR (acetone $d_6$): δ=5.96 (S, 2H—$CH_2C(NO_2)_3$), 2.93 (q, 2H, —$SCH_2$—), 1.28 (t, 3H, —$CH_3$).

Calc for $C_5H_7N_3O_8S$: C, 22.31, H, 2.62; N, 15.61; S, 11.91. Found: C, 22.19; H, 2.57; N, 15.30; S, 11.65.

EXAMPLE 2

S-ethyl 2-fluoro-2,2-dinitroethyl thiolcarbonate

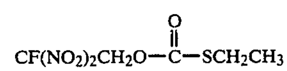

To a stirred solution of 7.7 g (0.05 mol) fluorodinitroethanol in 10 ml of methylene chloride was added 6.5 ml of ethyl chlorothiolformate and one ml of a 50% ferric chloride solution in nitromethane. A vigorous reaction immediately ensued that was essentially over in a few minutes. To insure complete reaction, stirring was continued for 30 minutes. The reaction mixture was taken up in methylene chloride and washed consecutively with 100 ml of dilute hydrochloric acid and five 100 ml portions of water. After drying with anhydrous magnesium sulfate and filtering, the organic solvents were removed in vacuo. The residue weighing 12.07 g (99.7%) was of >98% purity by GLC analysis.

H-NMR ($CDCl_3$): δ=5.24 (d, 2H, —$CH_2$—CF), 2.89 (q, 2H, —S—$CH_2$—), 1.30 (t, 3H, —$CH_3$).

Calcd for $C_5H_7FN_2O_6S$: C, 24.79; H, 2.91; F, 7.85; N, 11.57; S, 13.24. Found: C, 24.83; H, 2.96; F, 7.69; N, 11.68; S, 13.40.

EXAMPLE 3 bis(S-ethyl thiolcarbonate) of 2,2-dinitro-1,3-propandiol

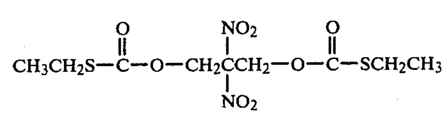

To a stirred solution of 4.0 g (0.024 mol) of 2,2-dinitropropan-1,3-diol in 25 ml of methylene chloride/nitromethane 4/1 was added 5.8 ml ethyl chlorothiolformate and one ml of a solution of 50% ferric chloride in nitromethane. After an initial vigorous reaction, the solution was stirred for an additional 30 minutes at ambient temperature. The solution was taken up in methylene chloride and washed with a 100 ml portion of dilute hydrochloric acid and five 100 ml portions of water. After drying and filtering, the solvent was removed in vacuo at 0.05 torr. The residue weighed 8.3 g (100%). The purity of the residue was >98% by GLC analysis.

H-NMR ($CDCl_3$): δ=5.08 (S, 4H, —O—$CH_2$—C($NO_2$)$_2$$CH_2$O—), 2.87 (d, 4H, —S—$CH_2$—), 1.29 (t, CH, —$CH_3$).

(Calc. for $C_9H_{14}N_2O_8S_2$: C, 31.57; H, 4.12; N, 8.19; S, 18.73. Found: C, 31.76; H, 4.30; N, 8.06; S, 18.77.

EXAMPLE 4

2-fluoro-2,2-dinitroethyl chloroformate

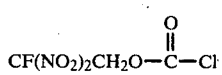

A solution of 13.82 g (0.057 mol) S-ethyl fluorodinitroethyl-thiolcarbonate in 50 ml of 1,2-dichloroethane and 20 ml of sulfuryl chloride was refluxed for 6 hours. After cooling, excess sulfuryl chloride and solvent was removed on a rotavac. The residue was distilled through a short column, 58° at 2 torr. To the yellowish distillate was added 2 ml cyclohexane and this was redistilled to give 11.59 g (94%) of product. GLC analysis indicated a purity of 99%.

I.R. (film): $\nu_{max}$=1780, 1605, 1310 $cm^{-1}$.

H-NMR ($CDCl_3$): δ=5.36 (d, FC—$CH_2$—).

EXAMPLE 5

2,2,2-trinitroethyl chloroformate

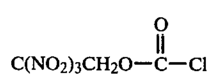

To a solution of S-ethyl trinitorethylthiolcarbonate (27.85 g, 0.098 mol) in 50 ml of 1,2-dichloroethane was added 30 ml of sulfuryl chloride. The reaction solution was refluxed for six hours, cooled, and volatiles removed in vacuo. The residue was distilled through a short path column, 78° at 0.8 torr, to give 24.23 g of product. GLC analysis indicated a purity of 96.5%; corr. yield was 97.4%.

I.R. (film): $\nu_{max}$=1783, 1608, 1300 $cm^{-1}$.

H-NMR ($CDCl_3$): δ=5.73 (S, —$CH_2$—).

EXAMPLE 6

2,2-dinitropropyl chloroformate

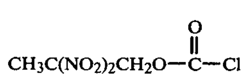

A solution of S-ethyl 2,2-dinitropropylthiolcarbonate in 50 ml of 1,2-dichloroethane and 20 ml of sulfuryl chloride was refluxed for 6 hours. After cooling and removal of volatiles in vacuo the residue was distilled through a short path column to give 10.65 g (90%) of product; bp 82° at 0.2 torr.

I.R. (film): $\nu_{max}$=1779, 1570, 1323 $cm^{-1}$

H-NMR ($CDCl_3$) δ=5.08 (S, 2H, —$CH_2$—), 2.25 (S, 3H, —$CH_3$).

EXAMPLE 7

1,3-bis(3,3,3-trinitroethyl carbonyldioxy)-2,2-dinitropropane

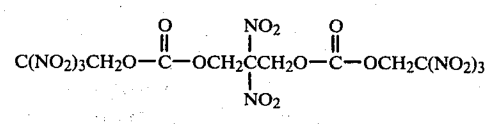

Pyridine (2.1 ml) was added to a slurry of 2,2-dinitropropan-1,3-diol in 50 ml of $CH_2Cl_2$ at 10° C. After the diol had dissolved, a solution of trinitroethyl chloroformate (6.46 g, 26.6 mmol) in 7 ml of methylene chloride was added dropwise with stirring. The temperature was held below 15° during the addition. The solution was then stirred for 3.5 hours. Volatiles were then removed and the residue was washed with dilute hydrochloric acid and water and then air dried. The solid was recrystallized from methylene chloride to give 5.1 g of product (83%), m.p. 154°-5°.

H-NMR (acetone-$d_6$): δ=5.97 (S, 4H, $CH_2C(NO_2)_3$), 5.40 (S, 4H, $CH_2$)

I.R. (fluorolube): $\nu_{max}$=1780 $cm^{-1}$.

EXAMPLE 8

2,2-dinitropropyl-3,3,3-trinitroethylcarbonate

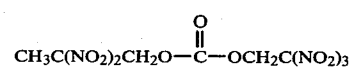

To a solution of trinitroethyl chloroformate (6.46 g, 26.5 mmol) and 2,2-dinitropropanol (4.5 g, 30 mmol) in 25 ml of methylene chloride was added dropwise a solution of pyridine (2.24 ml) in methylene chloride (7 ml) at or below 5°. Then the solution was stirred for 3 hr at ice bath temperature and at ambient temperature for an additional hour. The solution was taken up in methylene chloride and washed consecutively with 100 ml of dilute hydrochloric acid and five 100 ml portions of water. The organic layer was dried (magnesium sulfate), filtered, and the volatiles removed in vacuo. The solid residue was recrystalized from chloroform to give 5.68 g (60%) of product, m.p. 107°.

Calc. for $C_6H_7N_5O_{13}$: C, 20.18; H, 1.98; N, 19.61. Found: C, 19.87; H, 1.82; N, 19.85.

H-NMR ($CDCl_3$): δ=5.47 (S, 2H, $CH_2C(NO_2)_3$), 5.04 (S, 2H, O—$CH_2C(NO_2)_2$—), 2.20 (S, 3H, —$CH_3$).

I.R. (fluorolube mull): $\nu_{max}$=1777 $cm^{-1}$.

EXAMPLE 9

2,2-dinitropropyl-3-fluoro-3,3-dinitroethylcarbonate

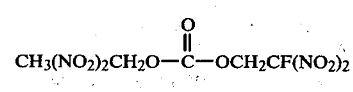

To a solution of dinitropropyl chloroformate (5.74 g, 0.027 mol) and fluorodinitroethanol (3.08 g, 0.02 mol) in 25 ml of methylene chloride at 4° was added with stirring a solution of pyridine (1.58 ml) in methylene chloride (9 ml). The rate of addition was controlled so that the temperature did not rise above 8°. After the addition was complete the reaction mixture was stirred for 3 hours at ice bath temperature and an additional 3 hours at ambient temperature. The reaction mixture was then transferred to a separatory funnel with 50 ml of methylene chloride and washed consecutively with 100 ml of dilute hydrochloric acid and four 100 ml portions of water. The organic layer was dried (magnesium sulfate) filtered and the solvents removed in vacuo. The residue was crystallized from chloroform to give 6.0 g of product, 91% based on fluorodinitroethanol, m.p. 66°.

Calc for $C_6H_7FN_4O_{11}$; C, 21.83; H, 2.14; F, 5.75; N 16.97. Found C, 21.98; H, 2.15; F, 6.00; N, 16.77.

H-NMR ($CDCl_3$): $\delta$=5.25 (d, 2H, $CH_2$—CF), 5.00 (S, 2H, $CH_2C(NO_2)_2$), 2.19 (S, 3H, —$CH_3$).

I.R. (fluorolube mull); $\nu_{max}$=1780 $cm^{-1}$.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A compound of the formula

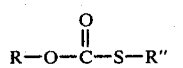

wherein R is selected from the group consisting of —$CH_2C(NO_2)_3$, —$CH_2CF(NO_2)_2$, —$CH_2CF_2(NO_2)$, —$CH_2CCl(NO_2)_2$, —$CH_2CF_3$, —$CH_2CCl_3$, —$CH_2C(NO_2)_2CH_3$, and —$CH_2CF_2CF_2H$, and wherein R″ is a lower alkyl group of from 1 to 6 carbon atoms.

2. The compound of claim 1 wherein R is —$CH_2C(NO_2)_3$.

3. The compound of claim 2 which is S-ethyl 2,2,2-trinitroethyl thiolcarbonate.

4. The compound of claim 1 wherein R is —$CH_2CF(NO_2)_2$.

5. The compound of claim 4 which is S-ethyl 2-fluoro-2,2-dinitroethyl thiolcarbonate.

6. The compound of claim 1 wherein R is —$CH_2CF_2(NO_2)$.

7. The compound of claim 6 which is S-ethyl 2,2-difluoro-2-nitroethyl thiolcarbonate.

8. The compound of claim 1 wherein R is —$CH_2CCl(NO_2)_2$.

9. The compound of claim 8 which is S-ethyl 2-chloro-2,2-dinitroethyl thiolcarbonate.

10. The compound of claim 1 wherein R is —$CH_2C(NO_2)_2CH_3$.

11. The compound of claim 10 which is S-ethyl 2,2-dinitropropyl thiolcarbonate.

12. A compound of the formula

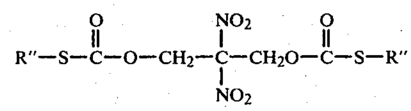

wherein R″ is a lower alkyl group of from 1 to 6 carbon atoms.

13. The compound of claim 12 which is

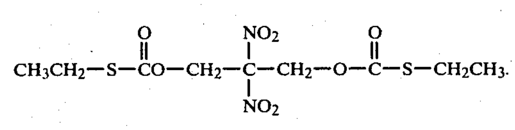

* * * * *